United States Patent [19]

Haugwitz et al.

[11] 4,136,174
[45] Jan. 23, 1979

[54] BENZIMIDAZOLECARBAMATES AND METHOD

[75] Inventors: Rudiger D. Haugwitz, Titusville; Peter C. Wade, Pennington, both of N.J.

[73] Assignee: E. R. Squibb & Sons, Inc., Princeton, N.J.

[21] Appl. No.: 870,391

[22] Filed: Jan. 18, 1978

[51] Int. Cl.² .................. A61K 31/695; C07F 7/10
[52] U.S. Cl. ........................... 424/184; 548/306
[58] Field of Search ..................... 424/184; 548/306

[56] References Cited

U.S. PATENT DOCUMENTS

| | | | |
|---|---|---|---|
| 3,574,845 | 4/1971 | Actor et al. | 548/306 |
| 3,578,676 | 5/1971 | Dunn | 548/306 |
| 3,682,952 | 8/1972 | Actor et al. | 548/306 |
| 3,694,455 | 9/1972 | Dunn | 548/306 |
| 3,738,993 | 6/1973 | Haugwitz et al. | 548/333 |
| 3,915,986 | 10/1975 | Gyurik et al. | 548/306 |
| 3,928,375 | 12/1975 | Düwel et al. | 548/306 |
| 3,929,821 | 12/1975 | Beard et al. | 548/306 |
| 3,929,822 | 12/1975 | Beard et al. | 548/306 |
| 3,929,823 | 12/1975 | Beard et al. | 548/306 |
| 3,929,824 | 12/1975 | Beard et al. | 548/306 |
| 3,935,209 | 1/1976 | Beard et al. | 548/306 |
| 3,954,791 | 5/1976 | Loewe et al. | 548/306 |
| 3,965,113 | 6/1976 | Beard et al. | 548/306 |
| 3,969,526 | 7/1976 | Gyurik et al. | 548/306 |
| 4,002,640 | 1/1977 | Beard et al. | 548/306 |
| 4,005,202 | 1/1977 | Beard et al. | 548/306 |
| 4,046,908 | 9/1977 | Haugwitz et al. | 548/306 |
| 4,093,732 | 6/1978 | Haugwitz et al. | 548/306 |

*Primary Examiner*—Natalie Trousof
*Attorney, Agent, or Firm*—Lawrence S. Levinson; Merle J. Smith; Burton Rodney

[57] ABSTRACT

Benzimidazolecarbamate derivatives are provided having the structure

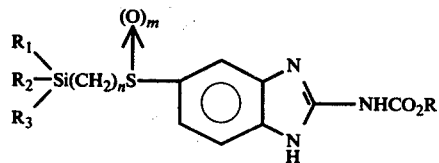

wherein R is lower alkyl, $R_1$, $R_2$ and $R_3$ may be the same or different and may be lower alkyl or lower alkoxy, m is 0, 1 or 2 and n is 1 to 5. These compounds are useful as anthelmintic agents.

14 Claims, No Drawings

BENZIMIDAZOLECARBAMATES AND METHOD

BACKGROUND OF THE INVENTION

Various benzimidazole compounds are known for their use as anthelmintic agents, such as disclosed in U.S. Pat. Nos. 3,929,821, 3,929,822, 3,929,823, 3,929,824, 3,935,209 3,965,113, 4,002,640 and 4,005,202 all to Beard et al and assigned to Syntex; 3,574,845 and 3,682,952 to Actor, 3,578,676 and 3,694,455 to Dunn, 3,915,986 and 3,969,526 to Gyurik, all assigned to Smith Kline; 3,738,993 to Haugwitz et al.

U.S. Pat. No. 4,002,640 discloses benzimidazole compounds which have the structure

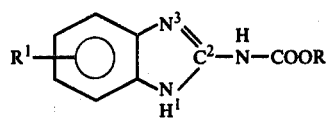

wherein R is lower alkyl having 1 to 4 carbon atoms, $R^1$ may be $-SR^5$, and $R^5$ may be lower alkenyl, wherein the double bond is not on the α-carbon. Specific compounds disclosed include 5(6)-(prop-2-en-1-ylthio)-2-carbomethoxyaminobenzimidazole, and 5(6)-(prop-2-en-1-ylsulfinyl)-2-carbomethoxyaminobenzimidazole. These compounds as well as the benzimidazoles disclosed in all of the aforementioned patents are said to be active perorally in the treatment of helminthiasis.

U.S. Pat. Nos. 3,954,791 to Loewe et al and 3,928,375 to Duwel et al, both assigned to Hoechst disclose 2-carbalkoxy-amino-benzimidazole-5(6)-phenyl ethers (and thioethers) which are said to be active perorally as well as subcutaneously.

DESCRIPTION OF THE INVENTION

The present invention relates to derivatives of benzimidazolecarbamates having the structure

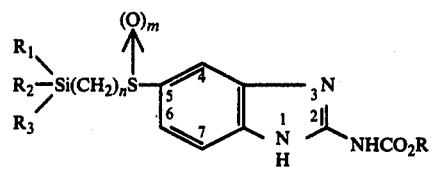

wherein R is lower alkyl, $R_1$, $R_2$ and $R_3$ may be the same or different and may be lower alkyl or lower alkoxy, m is 0, 1 or 2 and $(CH_2)_n$ represents an alkylene group having 1 to 5 carbons.

The term "lower alkyl" as used herein includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like. However, in the case of $R_1$, $R_2$ and $R_3$, only one or two lower alkyls of same may contain more than one branch.

The term "lower alkoxy" includes any of the above lower alkyl groups linked to an oxygen atom.

Preferred are those compounds wherein $R_1$, $R_2$ and $R_3$ are lower alkyl or $R_1$ and $R_2$ are lower alkyl and $R_3$ is lower alkoxy.

Most preferred are those compounds wherein R is methyl, ethyl or propyl, n is 1, m is 0 or 1 and $R_1$, $R_2$ and $R_3$ are each methyl, or two thereof are ethoxy and the other methyl, or each are ethoxy.

The compounds of structure I may be prepared according to the following reaction sequences.

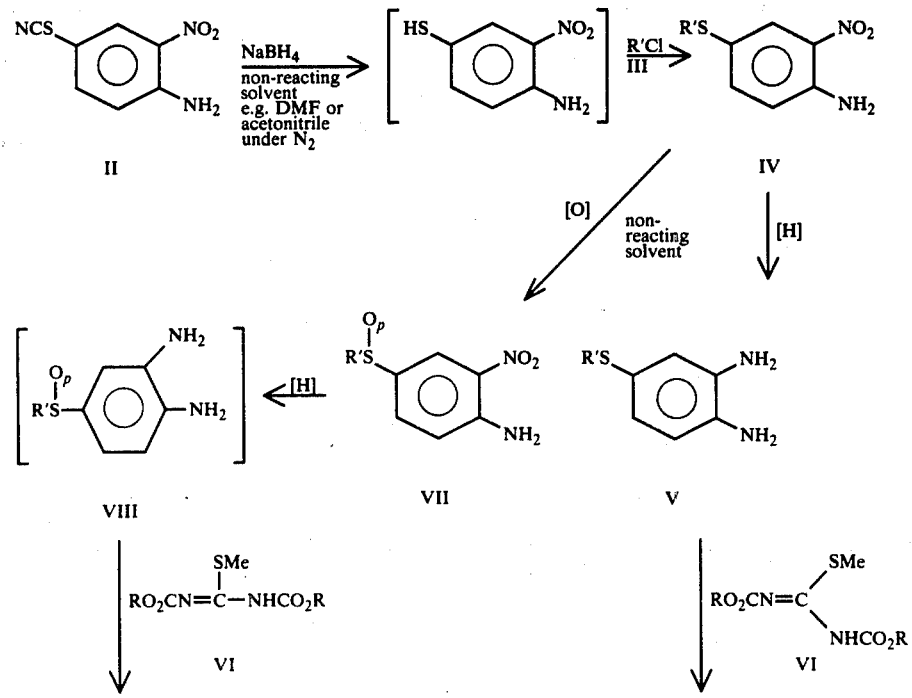

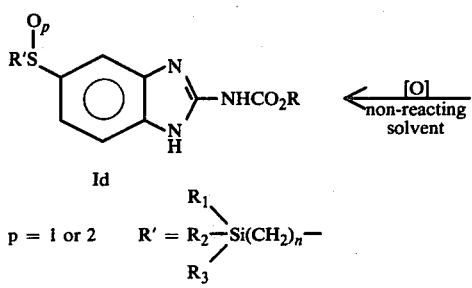

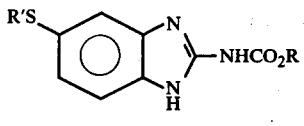

Id    Ia p = 1 or 2    R' = R₂—Si(CH₂)ₙ—
         R₁\
         R₃/

The compounds of structure I wherein m is 0, that is

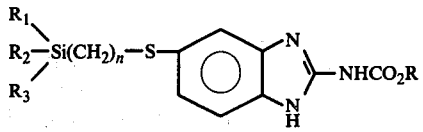

may be prepared by reacting 4-thiocyanato-2-nitroaniline II with sodium borohydride in the presence of a non-reacting solvent, such as dimethyl formamide or acetonitrile under nitrogen for a period ranging from about 0.5 to about 4 hours. Thereafter, a silane derivative III is admixed with the mixture with heating to form a silylalkylenethio-2-nitroaniline derivative IV.

The silylalkylenethio-2-nitroaniline derivative IV is then reduced employing conventional reduction techniques, for example, catalytically with hydrogen and platinum or chemically with dithionite, or zinc and acetic acid, to form the corresponding o-phenylenediamine V which is then reacted with an isothiourea of the structure VI in the presence of an alcohol solvent (ROH) or other non-reacting solvent, and optionally, an acid catalyst, such as acetic acid at temperatures ranging from about 50° to about 200° C., and preferably from about 80° to about 130° C., for one minute to 3 days, preferably for 1 to 24 hours, to form the formula Ia compounds.

The formula Ia compound may be oxidized to the corresponding sulfoxide Ib employing one equivalent of an oxidizing agent such as hydrogen peroxide in acetic acid, sodium meta periodate or m-chloroperbenzoic acid.

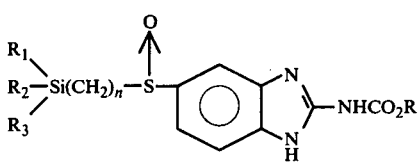

The sulfone

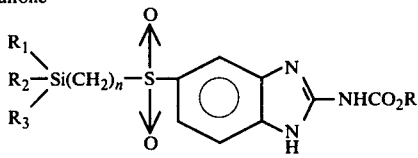

may be prepared by reacting the thio compound Ia with two or more equivalents of any of the above oxidizing agents; alternatively, the sulfone Ic may be prepared by reacting the sulfoxide Ib with one equivalent of any of the above oxidizing agents.

Compounds of structures Ib and Ic may also be prepared by oxidizing the formula IV silylalkylenethio-2-nitroaniline derivative with one or two or more equivalents of oxidizing agent to form a silylalkylenesulfinyl(or sulfonyl)-2-nitroaniline VII which is then reduced to the o-phenylenediamine VIII. The o-phenylenediamine VIII is then reacted with the thiourea VI in the presence of an alcohol solvent (ROH) or other non-reacting solvent to form the compound of structure Id (that is, Ib or Ic).

The starting materials employed in the above reactions are either known in the art or easily prepared according to conventional techniques.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with nontoxic, edible carrier to form a feed supplement, or be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5–25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

[5-[(Diethoxymethylsilylmethyl)thio]-1H-benzimidazol-2-yl]-carbamic acid, methyl ester A. 4-(Diethoxymethylsilylmethyl)thio-2-nitroaniline To a stirring solution of 25.3 g (0.13 mol) 4-thiocyanato-2-nitroaniline in 500 ml of acetonitrile under nitrogen is added 4.94 g (0.13 mol) of sodium borohydride in portions over 45 minutes at room temperature. The mixture is stirred for 2 hours and 25.0 g (0.137 mol) of chloromethylmethyldiethoxysilane is added and the mixture is refluxed overnight. The reaction mixture is cooled, filtered and the filtrate evaporated to dryness. The residue is extracted repeatedly with hot hexane to yield, on evaporation, 31 g of the title compound as a red oil. This is used without further purification.

B. 1,3-Bis(methoxycarbonyl)-S-methylisothiourea

To a solution of 11.2 g of 2-methyl-2-thiopseudourea sulfate in 200 ml of water at 0° C. there is added concurrently 260 ml of 25% NaOH and 160 ml of methylchloroformate at such a rate that the pH remains between 7 and 8 as monitored by a pH meter. After the addition is complete the mixture is stirred for an additional 2 hours at room temperature. Then 400 ml of water is added and the mixture is extracted with dichloromethane. The organic layers are combined, dried over magnesium sulfate, and evaporated in vacuo to give a white solid. Crystallization from methanol yields 60.4 g of the title B compound, m.p. 99°–101° C.

C. [5-[(Diethoxymethylsilylmethyl)thio]-1H-benzimidazol-2-yl]carbamic acid, methyl ester 7.9 g (0.028 mol) of the nitroaniline obtained in part A is hydrogenated at 60 psi in 225 ml of methanol with 0.8 g of platinum oxide catalyst. After 24 hours, the color is largely gone and thin layer chromatography shows the absence of starting material. The mixture is filtered and 5.7 g (0.028 mol) of 1,3-bis(methoxycarbonyl)-S-methylisothiourea (prepared in part B), and 0.1 ml of acetic acid added to the filtrate. The mixture is refluxed for 36 hours, cooled and allowed to stand in the freezer. The resulting crystals are filtered off and recrystallized (hot filtration) from cyclohexane to give 4.0 g of the title compound.

EXAMPLE 2

[5-[(Diethoxymethylsilylmethyl)sulfinyl]-1H-benzimidazol-2-yl]carbamic acid, methyl ester To an ice-cold solution of 40 mmol of [5-[(diethoxymethylsilylmethyl)thio]-1H-benzimidazol-2-yl]carbamic acid, methyl ester prepared as described in Example 1, in 150 ml methanol is added 8.98 g (42 mmol) sodium metaperiodate in 150 ml water. The resulting suspension is stirred at 5° C. for 42 hours, then partitioned between water and dichloromethane. The layers are separated and the aqueous layer re-extracted. The organic layers are combined and washed with saturated NaCl, dried, filtered and evaporated to yield a residue which is crystallized three times from acetonitrile to yield the title sulfinyl compound.

EXAMPLE 3

[5-[(Diethoxymethylsilylmethyl)sulfonyl]-1H-benzimidazol-2-yl]carbamic acid, methyl ester 0.00625 mole of [5-[(diethoxymethylsilylmethyl)thio]-1H-benzimidazol-2-yl]carbamic acid, methyl ester prepared as described in Example 1, is dissolved in 40 ml acetic acid and 40 ml chloroform, and cooled to −10° C. with an ice-methanol bath. To this is added 2 equivalents of m-chloroperbenzoic acid in 10 ml chloroform, all at once. Stirring is continued for three hours, allowing temperature to rise to room temperature. The solvent is removed in vacuo yielding an oil, which is digested with aqueous NaHCO$_3$. Solids are collected, washed with water, dried and crystallized from 1,2-dimethoxyethane to give the title sulfone.

EXAMPLE 4

N-[5-[[(Trimethylsilyl)methyl]thio]-2-benzimidazolyl]-carbamic acid, methyl ester A. 4-[(Trimethylsilyl)methylthio]-2-nitroaniline To a stirred solution of 1.95 g of 4-thiocyanato-2-nitroaniline in 40 ml of CH$_3$CN blanketed by nitrogen there is added in portions 0.5 g of NaBH$_4$. The stirring is continued for one hour. At this time the color of the reaction mixture changes from yellow to dark purple. 1.4 ml of chloromethyltrimethylsilane is added with a syringe and the mixture is refluxed overnight. The solvent is evaporated and the residue is exhaustively extracted with petroleum ether. Evaporation of the solvent yields 1.9 g of the title A compound as a red solid.

B. 4-[(Trimethylsilyl)methylthio]-o-phenylenediamine

A solution of 1.9 g of the above nitroaniline in 200 ml of methanol is catalytically reduced (60 psi) using 0.4 g PtO$_2$ as catalyst. Upon completion, the catalyst is filtered off and the filtrate is used at once for the next step.

C. N-[5-[[(Trimethylsilyl)methyl]thio]-2-benzimidazolyl]carbamic acid, methyl ester To the above filtrate (part B) there is added 2 g of 1,3-bis[methoxycarbonyl]-S-methylisothiourea (prepared as described in Example 1, part B), 7 drops of acetic acid and the mixture is refluxed for two hours. The solvent is evaporated and the residue extracted with ether. The ether insoluble part is crystallized from ethanol. The ether soluble material and the ethanol purified fraction are combined and recrystallized from ethanol to yield 0.7 g of the title compound, m.p. 189°–191°.

EXAMPLE 5

N-[5-[[Trimethylsilyl)methyl]sulfinyl]-2-benzimidazolyl]carbamic acid, methyl ester To an ice-cold solution of 40 mmol of [5-[[(trimethylsilyl)methyl]thio]-2-benzimidazolyl]carbamic acid, methyl ester prepared as described in Example 4, in 150 ml methanol is added 8.98 g (42 mmol) sodium metaperiodate in 150 ml water. The resulting suspension is stirred at 5° C. for 42 hours, then partitioned between water and dichloromethane. The layers are separated and the aqueous layer re-extracted. The organic layers are combined and washed with saturated NaCl, dried, filtered and evaporated to yield a residue which is crystallized three times from acetonitrile to yield the title fulfinyl compound.

EXAMPLE 6

N-[5-[[(Trimethylsilyl)methyl]sulfonyl]-2-benzimidazolyl]carbamic acid, methyl ester 0.00625 mole of N-[5-[[(trimethylsilyl)methyl]thio]-2-benzimidazolyl]carbamic acid, methyl ester prepared as described in Example 4, is dissolved in 40 ml acetic acid and 40 ml chloroform, and cooled to −10° C. with an ice-methanol bath. To this is added 2 equivalents of m-chloroperbenzoic acid in 10 ml chloroform, all at once. Stirring is continued for three hours, allowing temperature to rise to room temperature. The solvent is removed in vacuo yielding an oil, which is digested with aqueous NaHCO$_3$. Solids are collected, washed with water, dried and crystallized from 1,2-dimethoxyethane to give the title sulfone.

EXAMPLES 7 To 16

Following the procedure of Example 1 except substituting for chloromethylmethyldiethoxysilane, the compound shown in Table I, Column I below, and substituting for 1,3-bis-(methoxycarbonyl)-S-methylisothiourea, the compound shown in Column II, the compound shown in Column III is obtained.

TABLE I

| Ex. No. | (CH$_2$)$_n$ | R$^1$ | R$^2$ | R$^3$ | R | (CH$_2$)$_n$ R$^1$ R$^2$ R$^3$ R |
|---|---|---|---|---|---|---|
| 7. | CH$_2$ | CH$_3$ | C$_2$H$_5$ | C$_2$H$_5$ | CH$_3$ | as per Column I / as per Column II |
| 8. | CH$_2$ | C$_2$H$_5$ | CH$_3$ | CH$_3$ | C$_2$H$_5$ | |
| 9. | (CH$_2$)$_2$ | CH$_3$O | CH$_3$O | CH$_3$ | C$_2$H$_5$ | |
| 10. | (CH$_2$)$_3$ | C$_2$H$_5$O | C$_2$H$_5$O | C$_2$H$_5$O | CH$_3$ | |
| 11. | (CH$_2$)$_2$ | C$_3$H$_7$ | C$_2$H$_5$ | CH$_3$O | C$_2$H$_5$ | |
| 12. | CH$_2$ | CH$_3$ | CH$_3$O | CH$_3$ | C$_2$H$_5$ | |
| 13. | (CH$_2$)$_4$ | CH$_3$ | C$_2$H$_5$O | CH$_3$ | CH$_3$ | |
| 14. | (CH$_2$)$_2$ | C$_2$H$_5$ | CH$_3$ | C$_2$H$_5$ | C$_2$H$_5$ | |
| 15. | CH$_2$ | C$_3$H$_7$ | C$_2$H$_5$ | C$_2$H$_5$ | CH$_3$ | |
| 16. | CH$_2$ | CH$_3$O | CH$_3$O | CH$_3$O | CH$_3$ | |

EXAMPLES 17 To 26

Following the procedure of Example 2, the sulfides of Examples 7 to 16 shown in Column I of Table II below are oxidized to give the corresponding sulfoxides.

TABLE II

| Ex. No. | (CH$_2$)$_n$ | R$^1$ | R$^2$ | R$^3$ | R | (CH$_2$)$_n$ R$^1$ R$^2$ R$^3$ R |
|---|---|---|---|---|---|---|
| 17. | CH$_2$ | CH$_3$ | C$_2$H$_5$ | C$_2$H$_5$ | CH$_3$ | as per Column I |
| 18. | CH$_2$ | C$_2$H$_5$ | CH$_3$ | CH$_3$ | C$_2$H$_5$ | |
| 19. | (CH$_2$)$_2$ | CH$_3$O | CH$_3$O | CH$_3$ | C$_2$H$_5$ | |
| 20. | (CH$_2$)$_3$ | C$_2$H$_5$O | C$_2$H$_5$O | C$_2$H$_5$O | CH$_3$ | |
| 21. | (CH$_2$)$_2$ | C$_3$H$_7$ | C$_2$H$_5$ | CH$_3$O | C$_2$H$_5$ | |
| 22. | CH$_2$ | CH$_3$ | CH$_3$O | CH$_3$ | C$_2$H$_5$ | |
| 23. | (CH$_2$)$_4$ | CH$_3$ | C$_2$H$_5$O | CH$_3$ | CH$_3$ | |
| 24. | (CH$_2$)$_2$ | C$_2$H$_5$ | CH$_3$ | C$_2$H$_5$ | C$_2$H$_5$ | |
| 25. | CH$_2$ | C$_3$H$_7$ | C$_2$H$_5$ | C$_2$H$_5$ | CH$_3$ | |

TABLE II-continued

| | Column I | | | | | Column III | | | |
|---|---|---|---|---|---|---|---|---|---|
| Ex. No. | (CH₂)ₙ | R¹ | R² | R³ | R | (CH₂)ₙ | R¹ | R² | R³ | R |
| 26. | CH₂ | CH₃O | CH₃O | CH₃O | CH₃ | | | | | |

EXAMPLES 27 To 36

Following the procedure of Example 3, the sulfides of Examples 7 to 16 shown in Column I of Table III below are oxidized to give the corresponding sulfones.

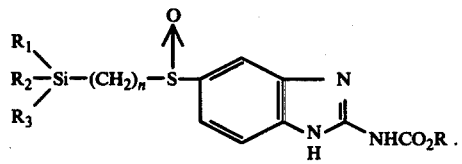

TABLE III

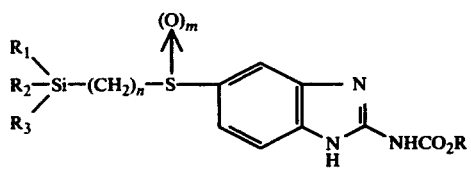

| Ex. No. | (CH₂)ₙ | R¹ | R² | R³ | R | (CH₂)ₙ R¹ R² R³ R |
|---|---|---|---|---|---|---|
| 27. | CH₂ | CH₃ | C₂H₅ | C₂H₅ | CH₃ | as per Column I |
| 28. | CH₂ | C₂H₅ | CH₃ | CH₃ | C₂H₅ | |
| 29. | (CH₂)₂ | CH₃O | CH₃O | CH₃ | C₂H₅ | |
| 30. | (CH₂)₃ | C₂H₅O | C₂H₅O | C₂H₅O | CH₃ | |
| 31. | (CH₂)₂ | C₃H₇ | C₂H₅ | CH₃O | C₂H₅ | |
| 32. | CH₂ | CH₃ | CH₃O | CH₃ | C₂H₅ | |
| 33. | (CH₂)₄ | CH₃ | C₂H₅O | CH₃ | CH₃ | |
| 34. | (CH₂)₂ | C₂H₅ | CH₃ | C₂H₅ | C₂H₅ | |
| 35. | CH₂ | C₃H₇ | C₂H₅ | C₂H₅ | CH₃ | |
| 36. | CH₂ | CH₃O | CH₃O | CH₃O | CH₃ | |

What is claimed is:

1. A compound of the structure

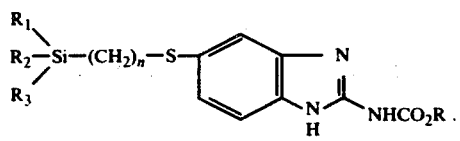

wherein R is lower alkyl containing 1 to 7 carbons, $R_1$, $R_2$ and $R_3$ may be the same or different and are selected from the group consisting of straight or branched chain lower alkyl containing 1 to 7 carbons or straight or branched chain lower alkoxy containing 1 to 7 carbons, provided that only one or two of $R_1$, $R_2$ and $R_3$ may contain more than one branch, m is 0, 1 or 2, and n is 1 to 5.

2. The compound as defined in claim 1 having the structure

R₁\
R₂—Si—(CH₂)ₙ—S—⟨benzimidazole⟩—NHCO₂R.
R₃/

3. The compound as defined in claim 1 having the structure

4. The compound as defined in claim 1 having the structure

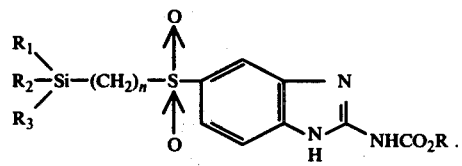

5. The compound as defined in claim 1 wherein $R_1$, $R_2$ and $R_3$ are lower alkyl.

6. The compound as defined in claim 1 wherein $R_1$ and $R_2$ are lower alkyl and $R_3$ is lower alkoxy.

7. The compound as defined in claim 1 having the name [5-[(diethoxymethylsilylmethyl)thio]-1H-benzimidazol-2-yl]carbamic acid, methyl ester.

8. The compound as defined in claim 1 having the name [5-[(diethoxymethylsilylmethyl)sulfinyl]-1H-benzimidazol-2-yl]carbamic acid, methyl ester.

9. The compound as defined in claim 1 having the name [5-[(diethoxymethylsilylmethyl)sulfonyl]-1H-benzimidazol-2-yl]carbamic acid, methyl ester.

10. The compound as defined in claim 1 having the name N-[5-[[(trimethylsilyl)methyl]thio]-2-benzimidazolyl]carbamic acid, methyl ester.

11. The compound as defined in claim 1 having the name N-[5-[[(trimethylsilyl)methyl]sulfinyl]-2-benzimidazolyl]carbamic acid, methyl ester.

12. The compound as defined in claim 1 having the name N-[5-[[(trimethylsilyl)methyl]sulfonyl]-2-benzimidazolyl]carbamic acid, methyl ester.

13. An anthelmintic composition comprising an effective amount of a compound as defined in claim 1, and a pharmaceutically acceptable carrier therefor.

14. A method for treating helminthiasis which comprises administering to a mammalian host an effective amount of the composition as defined in claim 13.

* * * * *

UNITED STATES PATENT AND TRADEMARK OFFICE
CERTIFICATE OF CORRECTION

PATENT NO. : 4,136,174

DATED : January 23, 1979

INVENTOR(S) : Rudiger D. Haugwitz et al.

It is certified that error appears in the above-identified patent and that said Letters Patent are hereby corrected as shown below:

Column 8, line 2, "fulfinyl" should read --sulfinyl--.
Table II, Column III, in the structure,

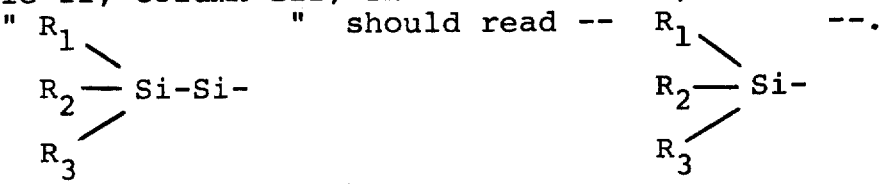

Signed and Sealed this

Twenty-ninth Day of May 1979

[SEAL]

Attest:

RUTH C. MASON
*Attesting Officer*

DONALD W. BANNER
*Commissioner of Patents and Trademarks*